United States Patent

Howarth et al.

[11] 4,088,656
[45] May 9, 1978

[54] OXOCLAVAMS

[75] Inventors: Thomas Trefor Howarth, Cranleigh; Irene Stirling, Worcester Park, both of England

[73] Assignee: Beecham Group Limited, Great Britain

[21] Appl. No.: 745,103

[22] Filed: Nov. 26, 1976

[30] Foreign Application Priority Data

Dec. 15, 1975 United Kingdom ............... 51241/75

[51] Int. Cl.² .......................................... C07D 498/04
[52] U.S. Cl. .............................. 260/307 FA; 424/246; 424/271; 424/272
[58] Field of Search ............................... 260/307 FA

[56] References Cited
PUBLICATIONS
Cole et al.- C. A. 84, 72635t (1976).

*Primary Examiner*—Raymond V. Rush
*Attorney, Agent, or Firm*—Jacobs & Jacobs

[57] ABSTRACT

The compound of the formula (II):

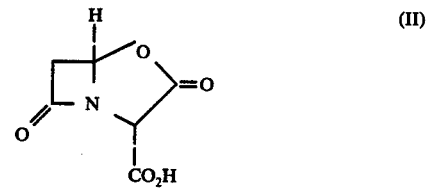

and its pharmaceutically acceptable salts and esters may be produced by ozonolysis of clavulanic acid and its derivatives. The compound has antibacterial and β-lactamase inhibiting activity.

12 Claims, No Drawings

OXOCLAVAMS

The present invention relates to novel β-lactam containing compounds, to their preparation and to compositions containing them, the said β-lactam containing compounds possessing β-lactamase inhibiting activity as well as a degree of antibacterial activity.

Belgian Pat. No. 827,926 discloses inter alia clavulanic acid which is the compound of the formula (I):

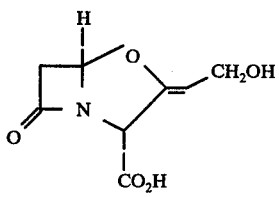

and its salts and esters. Clavulanic acid is a β-lactamase inhibitor and an antibacterial agent.

We have now discovered a distinct group of compounds which have the ability to inhibit certain β-lactamases such as those from certain strains of Pseudomonas.

Accordingly, the present invention provides the compound of the formula (II):

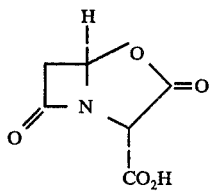

and pharmaceutically acceptable salts or esters thereof.

Suitably salts include lithium, sodium, potassium, calcium, magnesium, aluminum, ammonium and conventional substituted ammonium salts such as alkylamine, dialkylamine, trialkylamine and the like salts.

Particularly suitable salts include the alkali metal salts.

Preferred salts are the sodium and potassium salts. A particular suitable group of compounds of the formula (I) are those of the formula (III):

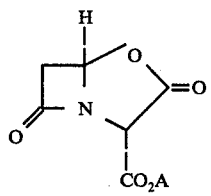

wherein A is a group such that $CO_2A$ is an ester group.

Suitably A is an inert organic group of up to 16 carbon atoms and most suitably an inert organic group of up to 12 carbon atoms.

Suitable values for A include alkyl, alkenyl, alkynyl, aryl or aralkyl groups, any of which may be substituted if desired.

Suitable substituents which may be included in the group A include halogen atoms and lower alkoxy, hydroxy, lower acyloxy or lower aryloxy groups.

When used herein the term 'lower' means the group contains up to 7 carbon atoms.

Thus, for example, A may be a methyl, ethyl, n-propyl, isopropyl, straight or branched butyl, pentyl, heptyl, octyl, nonyl, decyl, undecyl, dodecyl, vinyl, allyl, butenyl, cyclopropyl, cyclobutyl, cyclopentyl, cyclohexyl, cycloheptyl, cyclohexenyl, cyclohexadienyl, methylcyclopentyl, methylcyclohexyl, benzyl, benzhydryl, phenylethyl, naphthylmethyl, phenyl, naphthyl, propynyl, tolyl, 2-chloroethyl, 2,2,2-trichloroethyl, 2,2,2-trifluoroethyl, acetylmethyl, benzoylmethyl 2-methoxyethyl, p-chlorobenzyl, p-methoxybenzyl, p-nitrobenzyl, p-bromobenzyl, m-chlorobenzyl, 6-methoxynaphthyl-2-methyl, p-chlorophenyl or p-methoxyphenyl group.

A preferred group of compounds of the formula (III) are those wherein A is a group of the sub-formulae (a) – (d):

$CA_1A_2$—X—CO—$A_3$ (a)

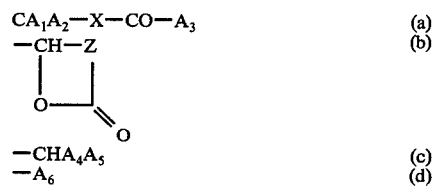

—$CHA_4A_5$ (c)
—$A_6$ (d)

wherein $A_1$ is a hydrogen atom or a methyl group; $A_2$ is a hydrogen atom or a $C_{1-4}$alkyl, phenyl or benzyl group; $A_3$ is a lower alkyl, lower alkyloxy, aryl or $C_{7-11}$ aralkyl group; X is oxygen or sulphur; Z is a divalent organic group; $A_4$ is a hydrogen atom or an inert aryl group; $A_5$ is an inert aryl group; $A_6$ is a hydrocarbon group of 1 to 9 carbon atoms optionally substituted by halogen atoms or by lower alkyl, lower acyl, lower etherified or acylated hydroxy groups.

In the above sub-formulae most suitably $A_1$ is a hydrogen atom; $A_2$ is a hydrogen atom or a methyl group; $A_3$ is a methyl, butyl or phenyl group X is oxygen; Z is —$CH_2CH_2$—, —CH=CH—,

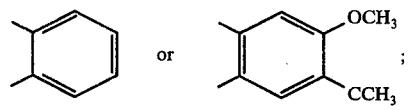

$A_4$ is hydrogen, phenyl, tolyl, halophenyl or methoxyphenyl group; $A_5$ is a phenyl, tolyl, halophenyl or methoxyphenyl group and $A_6$ is a hydrocarbon group of 1 to 6 carbon atoms optionally substituted by Cl, Br, I, $CF_3$, $C(CH_3)_3$, methoxy, acetyl, benzoyl or acetoxy groups.

A particularly preferred group of compounds of the formula (III) are those wherein A is a benzyl, naphthylmethyl or benzhydryl group or such a group substituted by one or more Cl, Br or I atoms or by nitro, $CF_3$ or methoxy groups.

Preferably A is a benzyl group or a p-methoxybenzyl group.

Belgium Pat. No. 827,926 may be inspected for other suitable ester groups.

In a composition aspect, the present invention provides a pharmaceutical composition which comprises a compound of the formula (II) as hereinbefore described. Such compositions will also comprise a pharmaceutically acceptable carrier.

The composition of this invention will normally be adapted for administration to humans and other mammals, for example, in conventional modes of treatment of diseases of the urinary tract.

Suitable forms of the compositions of this invention include tablets, capsules, creams, syrups, suspensions, solutions, reconstitutable powders, and sterile forms suitable for injection or infusion may be used. Such compositions may contain conventional pharmaceutically acceptable materials such as diluents, binders, colors, flavors, preservatives, disintegrants and the like in accordance with conventional pharmaceutical practice.

The compound of formula (II) may be present in the composition as sole therapeutic agent or it may be present together with other therapeutic agents such as a penicillin or cephalosporin antibiotic. Thus, suitable penicillin or cephalosporin antibiotics for inclusion in the composition of this invention include carbenicillin, ticarcillin, and their salts and in vivo hydrolyzable esters such as the phenyl, tolyl and indanyl esters.

When present in a pharmaceutical composition together with a penicillin or cephalosporin, the ratio of the compound of formula (II) present to penicillin or cephalosporin present may be from, for example, 10 : 1 to 1 : 3 and advantegeously may be from 5 : 1 to 1 : 2, for example, 3 : 1 to 1 : 1.

The total quantity of antibacterial agents present in any unit dosage form will normally be between 250 and 5000 mg and will usually be between 1000 and 3000 mg.

Normally between 500 and 10,000 mg of the compositions of the invention will be administered each day of treatment but more usually between 1000 and 5000 mg of the compositions of the invention will be administered per day. However, for the treatment of severe systemic infections or infections of particularly intransigent organisms, higher doses may be used in accordance with clinical practice.

The present invention also provides a process for the preparation of a compound of the formula (II) which process comprises the ozonolysis of a compound of the formula (IV):

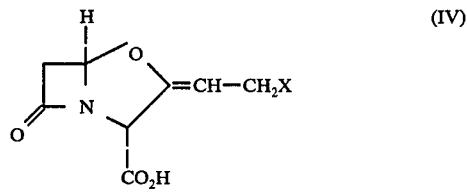

(IV)

or a salt or ester thereof wherein X is a hydrogen atom or a hydroxy or acyloxy group containing up to 16 carbon atoms with ozone. Normally the compound of the formula (IV) will be of the formula (V):

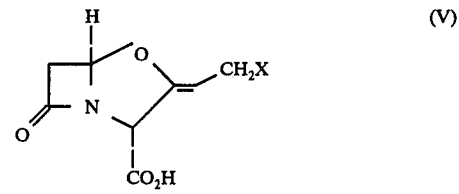

(V)

or a salt or ester thereof.

Suitably X is a hydrogen atom or a hydroxy group or an acyloxy group of the sub-formula:

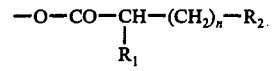

wherein $n$ is 0 or an integer from 1 to 6; $R_1$ is a hydrogen atom or a phenyl or phenoxy group and $R_2$ is a hydrogen or halogen atom or a $C_{1-4}$ alkyl, $C_{1-4}$ alkoxy or $CO_2R_3$ group where $R_3$ is a hydrocarbon group of 1 to 8 carbon atoms.

Most suitably X is a hydrogen atom or a hydroxyl group.

Preferably X is a hydroxy group.

This reaction is normally carried out in a solvent inert under the reaction conditions, such as methylene chloride, carbon tetrachloride or other conventional solvents.

This reaction is normally carried out at a depressed temperature, for example, suitably $-10°$ to $-90°$, most suitably $-30°$ to $-80°$ and preferably $-50°$ to $-70°$.

The resulting product from this reaction may be purified by conventional means, for example chromatography or distillation for a non-solid product or recrystallisation for a solid product. We have found column chromatography on silica gel a suitable method of chromatographic purification.

The carboxylic acid derived function at the 2- position of the compounds of the formula (II) may be converted to another carboxylic acid derived function by conventional methods well known to those skilled in the art.

Thus, when there is a free carboxylic acid group at the 2- position this may be converted to an ester group by reaction with an alcohol AOH wherein A is as defined in relation to formula (III) in the presence of a condensation promoting agent, such as dicyclohexylcarbodiimide, or by reaction with a diazocompound, such as diazomethane or alternatively it may be converted into a salt by treatment with base, such as sodium or potassium bicarbonate.

A salt of a compound of the formula (II) may be converted into an ester by a conventional nucleophilic substitution reaction by reaction with a compound AQ wherein A is as defined in relation to formula (III) and Q is a good leaving group such as Cl, Br, I, $OSO_2CH_3$, $OSO_2C_6H_4CH_3$ or the like.

The following example is illustrative of the invention:

EXAMPLE 1

Preparation of Benzyl 4-oxa,-3,7-dioxo-2-methyl-1-azabicyclo [3.2.0.] heptane-2-carboxylate

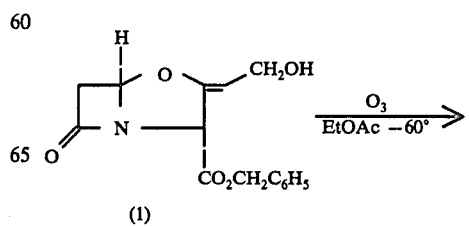

(1)

-continued

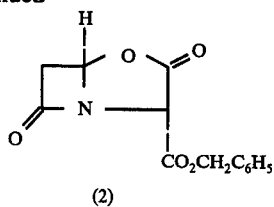

(2)

A solution of benzyl clavulanate (1) in ethyl acetate was treated with ozone at −60°. When the reaction was complete (1½ hours) nitrogen was bubbled through the solution and the temperature was allowed to rise slowly to room temperature. The solution was washed with water, dried over magnesium sulphate and the solvent removed. Purification by silica gel chromatography and crystallisation from ethanol gave the product (2) as a crystalline solid in 65% yield; m.p. 57° C, i.r. (Nujol) 1820, 1785, 1760 cm$^{-1}$. n.m.r. (CDCl$_3$): 3.22 (1H, dd, J 17 Hz, J' 1 Hz, 6β-H); 3.68 (1H, dd J 17 Hz, J' 3 Hz, 6α-H); 4.92 (1H, s, CHCO$_2$CH$_2$C$_6$H$_5$); 5.23 (2H, s, CO$_2$CH$_2$C$_6$H$_5$); 5.77 (1H, dd, J 3 Hz, J' 1 Hz, 5-H) and 7.36δ (5H, s, C$_6$H$_5$). The mass spectrum showed a molecular ion at 261. (C$_{13}$H$_{11}$NO$_5$ requires 261).

EXAMPLE 2 p-Bromobenzyl 3,7-dioxo-1-aza-4-oxabicyclo[3,2,0]-heptane-2-carboxylate

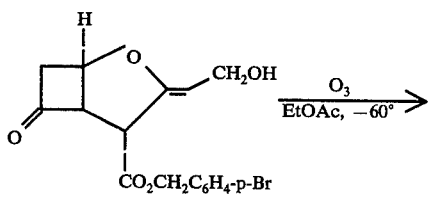

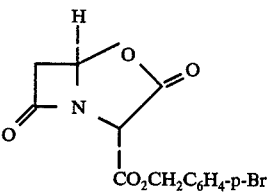

p-Bromobenzyl clavulanate (150 mg) was dissolved in ethyl acetate and treated with ozone at −60°. After 1 hour the starting materials had disappeared (thin layer chromatography) and the solution was saturated with ozone. Nitrogen was bubbled through the solution which was then washed with water, dried and evaporated. The resulting white solid was recrystallized from dichloromethane/petroleum ether (60°–80°) and was obtained as colorless needles in 71% yield; m.p. 105.5°–106° i.r. (Nujol) 1810–1790, 1665cm$^{-1}$; n.m.r. (CDCl$_3$) 3.23 (1H, dd, J 17.5Hz, J 1Hz, 6β-H) 3.63 (1H, dd, J 17.5Hz, J 3Hz, 6α-H) 4.88 (1H,s, CHCO$_2$CH$_2$C$_6$H$_4$-p-Br) 5.16 (2H,s,CH$_2$C$_6$H$_4$-p-Br) 5.73 (1H, dd, J 3Hz, J 1H2,5-H 7.18,7.48(4H,ABq, J 9Hz, aromatic-H). The mass spectrum exhibited a molecular ion m/e 338.97435 (C$_{13}$H$_{10}$$^{79}$BrNO$_5$ requires 338.97428) [α]$_D^{25}$ = + 141° (C 1.1; MeOH).

EXAMPLE 3

3,7-Dioxo-1-aza-4-oxabicyclo[3,2,0] heptane-2-carboxylic acid potassium salt

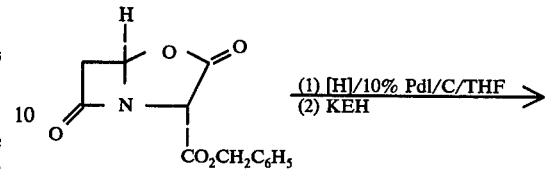

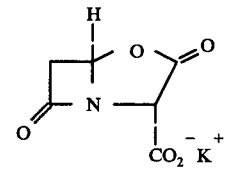

The ester (200 mg) was dissolved in dry redistilled tetrahydrofuran (10ml) and hydrogenated at normal temperature and pressure, using 10% palladium/charcoal as catalyst (70mg) for 30 minutes. The catalyst was immediately filtered off and the filtrate treated with a solution of potassium ethylhexanoate (1 equivalent) in tetrahydrofuran. Addition of ether to the solution precipitated the potassium salt of the bicyclic lactone. Further trituration and decantation with ether gave the desired product as an off-white solid in 62% yield.

i.r. (KBr) 2900–3600(b), 1750–1810(b), 1560–1650(b) cm$^{-1}$ i.r. (Nujol) 2500–3700(b), 1740–1815(b), 1560–1680(b) cm$^{-1}$

EXAMPLE 4

Methyl 3,7-dioxo-1-aza-4-oxabicyclo[3,3,0] heptane-2carboxylate

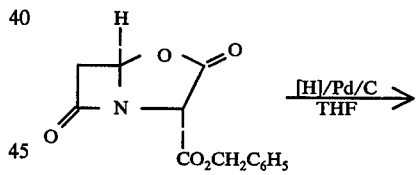

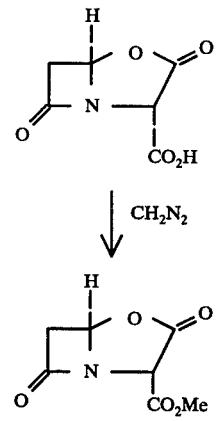

The benzyl ester (261 mg) in tetrahydrofuran (10ml) was hydrogenolyzed at normal temperature and pressure over 10% palladium or charcoal (80mg) for 30 minutes. The catalyst was filtered off and the filtrate treated with excess diazomethane in ether. The solvent was removed in vacuo to give an oil which was purified by column. Chromtography on silica gel using cyclohexane and ethyl acetate as eluants. The desired product was obtained as a colorless oil in 40% yield.

i.r. (film) 1800 (b), 1750 cm$^{-1}$.

n.m.r. (CDCl$_3$) 3.26 (1H, dd, J 17Hz, J 0.9Hz, 6β-H) 3.67 (1H,dd,J 17Hz,

J 3Hz, 6α-H) 3.81 (3H,s,CO$_2$CH$_3$ 4.88 (1H,s,CH CO$_2$CH$_3$)5.77 (1H,d,J 3Hz, 5-H). Mass spectrum showed a molecular ion at m/e 185 (C$_7$H$_7$NO$_5$ requires 185).

It should be noted that the free acid was present in the tetrahydrofuran solution prior to esterification.

EXAMPLE 5

3-Phthalidye 3,7-dioxo-1-aza-4-oxabicyclo [3,2,] heptane-2-carboxylate.

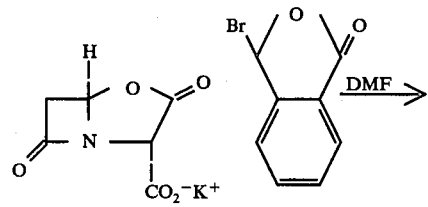

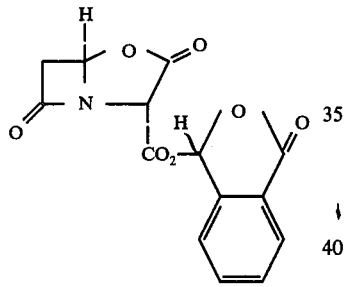

The potassium salt (50mg) was dissolved in dimethylformamide (10ml) and treated with 3-bromo-phthalide. The solution was stirred for 3 hours at room temperature, ethyl acetate (10ml), cyclohexane (5ml) and water (10ml) were added. The organic phase was separated washed with water, dried over magnesium sulphate and evaporated to yield a yellow gum (50%) yield) i.r. (film) 1730, 1760, 1810 cm$^{-1}$.

What is claimed is:

1. The compound of the formula (II):

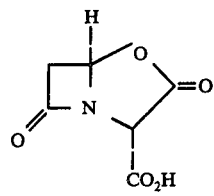

or a pharmaceutically acceptable salt thereof.

2. The compound according to claim 1 of the formula (II):

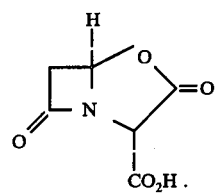

3. A pharmaceutically acceptable salt of the compound of claim 1.

4. The lithium, potassium, sodium, calcium, magnesium, ammonium, alkylammonium, dialkylammonium or trialkylammonium salt of the compound of the formula

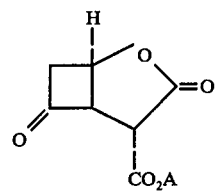

5. An alkali metal salt of the compound of claim 4.
6. The sodium salt of the compound of claim 4.
7. The potassium salt of the compound of claim 1.
8. An ester of the formula (III):

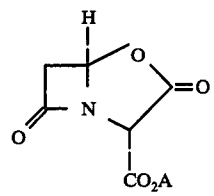

wherein A is methyl, ethyl, n-propyl, isopropyl, straight or branched butyl, pentyl, heptyl, octyl, nonyl, decyl, undecyl, dodecyl, vinyl, allyl, butenyl, cyclopropyl, cyclobutyl, cyclopentyl, cyclohexyl, cycloheptyl, cyclohexenyl, cyclohexadienyl, methylcyclopentyl, methylcyclohexyl, benzyl, benzhydryl, phenylethyl, naphthylmethyl, phenyl, naphthyl, propynyl, tolyl, 2-chloroethyl, 2,2,2-trichloroethyl, 2,2,2-trifluoroethyl, acetylmethyl, benzoylmethyl, 2-methoxyethyl, p-chlorobenzyl, p-methoxybenzyl, p-nitrobenzyl, p-bromobenzyl, m-chlorobenzyl, 6-methoxynaphthyl-2-methyl, p-chlorophenyl or p-methoxyphenyl.

9. An ester of the formula (III):

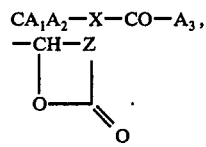

wherein A is a group of the formula:

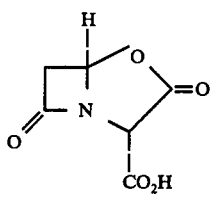

-continued $$-CHA_4A_5 \text{ or}$$
$$A_6$$

wherein $A_1$ is hydrogen; $A_2$ is hydrogen or methyl; $A_3$ is methyl, butyl, or phenyl; X is oxygen; Z is —CH$_2$CH$_2$—, —CH=CH—,

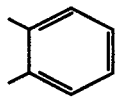

or

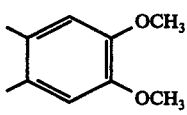

$A_4$ is hydrogen, phenyl, tolyl, halophenyl or methoxyphenyl; $A_5$ is phenyl, tolyl, halophenyl or methoxyphenyl; and $A_6$ is a hydrocarbon of 1 to 6 carbon atoms unsubstituted or substituted by Cl, Br, I, CF$_3$, C(CH$_3$)$_3$, methoxy, acetyl, benzoyl or acetoxy.

10. An ester of the formula

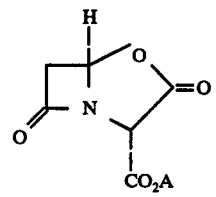

wherein A is benzyl, naphthylmethyl or benzhydryl unsubstituted or substituted by Cl, Br, I, nitro, CF$_3$ or methoxy.

11. The ester according to claim 8 wherein A is benzyl.

12. The ester according to claim 8 wherein A is p-methoxybenzyl.

* * * * *